United States Patent
Baral

(10) Patent No.: US 9,999,182 B2
(45) Date of Patent: Jun. 19, 2018

(54) MACHINE HARVESTABLE PEPPER

(71) Applicant: Vilmorin & CIE, Paris (FR)

(72) Inventor: Jit Baral, Davis, CA (US)

(73) Assignee: VILMORIN & CIE, Paris (FR)

( * ) Notice: Subject to any disclaimer, the term of this patent is extended or adjusted under 35 U.S.C. 154(b) by 139 days.

(21) Appl. No.: 14/776,297

(22) PCT Filed: Mar. 17, 2014

(86) PCT No.: PCT/US2014/030302
§ 371 (c)(1),
(2) Date: Sep. 14, 2015

(87) PCT Pub. No.: WO2014/145514
PCT Pub. Date: Sep. 18, 2014

(65) Prior Publication Data
US 2016/0029583 A1 Feb. 4, 2016

Related U.S. Application Data

(60) Provisional application No. 61/792,299, filed on Mar. 15, 2013.

(51) Int. Cl.
*A01H 5/08* (2018.01)
*A01D 45/00* (2018.01)
*A01G 1/00* (2006.01)
*A01H 1/02* (2006.01)

(52) U.S. Cl.
CPC .............. *A01H 5/08* (2013.01); *A01D 45/00* (2013.01); *A01G 1/001* (2013.01); *A01G 22/00* (2018.02); *A01H 1/02* (2013.01)

(58) Field of Classification Search
None
See application file for complete search history.

(56) References Cited

U.S. PATENT DOCUMENTS

| | | | | |
|---|---|---|---|---|
| 6,338,236 B1 * | 1/2002 | Rodriguez | ............. | A01D 45/00 56/13.2 |
| 8,158,866 B2 * | 4/2012 | McCarthy | ............... | A01H 5/08 435/430.1 |
| 2004/0268448 A1 | 12/2004 | Levy et al. | | |
| 2010/0115657 A1 * | 5/2010 | McCarthy | ............... | A01H 5/08 800/268 |
| 2011/0030082 A1 * | 2/2011 | Berke | ...................... | A01H 5/08 800/260 |
| 2013/0024963 A1 * | 1/2013 | Berke | ...................... | A01H 5/08 800/260 |

OTHER PUBLICATIONS

Shah et al. Progressive Horticulture 18 (3-4): 270-272 (1986).*
Walker et al. HortScience 45(8): S145-S146 (2010).*
Wang et al. HortScience 41(5): 1169-1187 (2006).*
Funk et al. International Journal of Vegetable Science 17(3): 269-309 (2011).*
Marshall, D. Capsicum and Eggplant Newsletter 16: 15-27 (1997).*
Wall et al., Yield and quality of machine harvested red chile peppers. Hort Technology. Apr.-Jun. 2003. vol. 13. No. 2. pp. 296-302.
Marshall. Designing peppers for mechanical harvest. The Chile Pepper Institute, 1998. vol. 7, No. 2. pp. 1-8.
Cooksey et al., Plant morphology and yield of paprika pepper in response to method of stand establishment. HortScience, Nov. 1994. vol. 29. No. 11. pp. 1282-1284.
Kahn et al., Within-row spacing effects on traits of importance to mechanical harvest in paprika-type peppers. Scientia Horticulturae. Mar. 31, 1997. vol. 69, No. 1-2. pp. 31-39.
PCT Search Report, PCT Application No. PCT/US14/30302, dated Aug. 18, 2014, 4 pages.

* cited by examiner

*Primary Examiner* — David T Fox
(74) *Attorney, Agent, or Firm* — Cooley LLP

(57) ABSTRACT

The present invention provides pepper ideotypes and pepper plants with machine harvestable traits combined with desirable agronomic traits. The present invention also provides methods of making such plants and methods of using such plants to produce additional machine harvestable pepper plants.

15 Claims, 2 Drawing Sheets

A. Blocky type pepper, whereas the length of the fruit is about the same as the width of the fruit B. Half long type pepper whereas the length of the fruit is about 1.2 to 1.5 the width of the fruit C. ¾ long type pepper whereas the length of the fruit is more than about 1.5 the width of the fruit, (often referred as lamuyo types fruit)

1. Short strong stem to withstand heavy fruit load
2. Wider crotch angle for lateral branching
3. Determinant habit, no continuous growth axis
4. Short internode
5. Easy destemming
6. Canopy angle

MACHINE HARVESTABLE PEPPER

CROSS-REFERENCE TO RELATED APPLICATIONS

This application is a national stage of International Patent Application No. PCT/US2014/030302, filed on Mar. 17, 2014, which claims the benefit of U.S. provisional application No. 61/792,299 filed on Mar. 15, 2013, each of which is hereby incorporated by reference in its entirety including all descriptions, references, figures, and claims for all purposes.

TECHNICAL FIELD

The present invention relates to plant breeding and methods of agronomical and horticultural production. More specifically, the present invention relates to agriculturally useful pepper plants that are specifically bred for mechanical harvesting and to methods of producing, processing and using such plants and their parts, including their fruit.

BACKGROUND

Existing pepper varieties are suitable for manual harvesting, which often requires growers to send crews into the field multiple times. Labor cost for manual harvest for pepper accounts for more than 50% of total production cost in the United States (Hawkes and Libbin, 2000, *Crop cost and return estimates in New Mexico,* 1998, New Mexico Agric. Expt. Station, Las Cruces, N. Mex.) but decreases to less than 10% of production costs with mechanical harvest (Eastman et al., 1997, *Impact of increasing wages on New Mexico chile production,* New Mexico Agric. Expt. Station Res. Report No. 714, Las Cruces, N. Mex.). A pepper plant must possess specific attributes for mechanical harvesting. Currently, there are no genotypes that have been specifically bred for mechanical harvesting for many of the commercially important pepper varieties. Existing varieties have indeterminate growth habit resulting in continuous fruit set.

Work on adapting or developing machines specific for the mechanical harvesting of chili peppers has been on-going at least from the early 1980's (see, e.g., Funk et al., 2011, *A systems approach to chile harvest mechanization,* International Journal of Vegetable Science, 17:296-309). To date the mainstream machine-solution research activities to harvest fresh pepper have focused on developing machines that are suitable to existing pepper ideotypes. Thus, past approaches have been focused on designing a machine based on existing crop architecture (e.g., in-determinant habit, distributive fruit set, multiple picking), rather then breeding peppers for adaptability for easier and more reliable mechanical harvesting. Assuming indeterminate growth habit of existing varieties, non destructive multiple-picking type of machines have been tested but have not been widely accepted by pepper growers and producers.

The main focus of past breeding attempts to adapt peppers to mechanical harvest has focused almost exclusively on red paprika type peppers. Almost all fruit of commercially grown red paprika peppers turn red at the end of the season, even immature fruit, and physical damage to the pod, therefore, does not matter that much as they go directly to the dryer anyway.

Attempts have also been made to adapt the machines used for harvesting red paprika peppers to see if they could be used for harvesting other types of peppers, such as green Jalapeño peppers. This approach has proven impractical and economically unviable since doing so requires multiple harvests for a single field and there is a huge risk of subsequent disease outbreak between the harvests due to the physical damage to the plant by the harvesters. Currently, there is insufficient research publicly available on the genetic controls of destemming and pod detachment force as well as determinant plant growth habit, all of which are important characteristics to consider in designing a machine-harvestable pepper plant.

The current invention meets a long felt need for a pepper plant ideotype suitable for machine harvesting and provides new elite pepper varieties useful for mechanical harvesting combined with other highly desirable agronomic traits.

SUMMARY OF THE INVENTION

The present invention provides machine harvestable pepper plants or parts thereof comprising the following phenotypic characteristics when compared to a check pepper plant of the same pepper species and type: determinant plant growth habit, high yield, optimal canopy angle, and higher number of pre-bifurcation branches. The present invention provides such machine harvestable pepper plants further comprising one or more of the following phenotypic characteristics when compared to the check pepper plant of the same species and type: higher resistance to fruit breaking, higher branching density, wider branching angle, stronger stem, more uniform maturity, shorter internodes, optimal width to height ratios, high total harvesting efficiency, optimal fruit maturity at harvest, increased fruit concentration, optimal pod detachment force, commercially acceptable fruit weight, commercially acceptable fruit wall thickness, easy destemming fruit, and high yield to biomass percent. A suitable check pepper plant for such a comparison is any commercially grown pepper plant having the same pepper fruit type as the machine harvestable pepper plant of the present invention. As used herein, the term "same pepper fruit type" refers to that of any two pepper plants being compared that have the same or similar type of pepper fruits. For example, any two pepper plants being compared can have long horn shape fruits (e.g., Jalapeño type), blocky type fruits (e.g., bell pepper type), ¾ long type fruits, half long type fruits (e.g., Serrano type) or any other pepper fruit shapes.

In one embodiment of the present invention, the machine harvestable pepper plants of present invention are of the species *Capsicum annuum*. In some embodiments of the present invention, the machine harvestable pepper plants are sweet Jalapeño pepper plants or hot Jalapeño pepper plants.

The present invention provides methods of harvesting pepper fruit comprising using a machine to harvest the fruit of pepper plants grown in a field until ready for harvesting of the fruit, wherein the pepper plants are the machine harvestable pepper plants of the present invention. The present invention further provides such methods where the harvesting machine is a tomato harvesting machine. In addition, the present invention provides such methods wherein the pepper field is at least one half acre in size.

The present invention provides pepper plants designated 'S5017', and S5082 or part thereof, a representative sample of the seeds of which have been deposited on Mar. 13, 2014, under ATCC Accession Numbers PTA-121088 and PTA-121087, respectively. The present invention provides the seed, ovules, pollen or fruit of the pepper plants of the present invention. The present invention further provides pepper plants having all of the morphological and physiological characteristics of the machine harvestable pepper plants of the present invention, e.g. pepper plants having all of the morphological and physiological characteristics of the machine harvestable pepper plants S5017 and/or S5082. The present invention provides the seed, ovules, pollen or fruit of pepper plants having all of the morphological and physiological characteristics of the machine harvestable pepper plants of the present invention, e.g. pepper plants having all of the morphological and physiological characteristics of the machine harvestable pepper plants S5017 and/or S5082. The present invention further comprises offspring of the machine harvestable pepper plants of the present invention, said offspring having at least determinant plant growth habit, high yield, optimal canopy angle and pre-bifurcation branches.

The present invention also provides machine harvestable pepper plants, or parts thereof, wherein the plant, or part thereof, have been transformed so that its genetic material contains one or more transgenes operably linked to one or more regulatory elements.

In some embodiments, the check variety of the same type is selected from the group consisting of P115, P105, 5807, 5810, Mammoth and Bravo.

The present invention also provides for asexually reproduced pepper plants produced via asexual reproduction of the machine harvestable pepper plants of the present invention. The present invention further provides regenerable pepper plant parts capable of producing a pepper plant having all of the morphological and physiological characteristics of the machine harvestable pepper plants of the present invention.

The present invention also provides tissue culture of regenerable cells produced from the machine harvestable pepper plants, or parts thereof, of the present invention. The present invention also provides machine harvestable pepper plants regenerated from a tissue culture of the plants, or parts thereof, of machine harvestable pepper plants of the present invention.

The present invention also provides methods for producing pepper seed comprising crossing the machine harvestable pepper plants of the present invention with itself or another pepper plant, and harvesting the resultant seed. The present invention further provides such methods which include growing the resultant seed to produce one or more progeny pepper plants, breeding from one or more of said progeny pepper plants to produce progeny seed, and harvesting said progeny seed. In addition, the present invention provides such methods further comprising growing said progeny seed, breeding from the resultant pepper plants to produce seed, and harvesting said seed, over 1, 2, 3, 4, 5, 6 or more generations.

In some embodiments, the present invention teaches a machine harvestable pepper plant, wherein said plant has determinate growth habit and at least three of the further phenotypic traits including: (i) a pepper yield at least 19% higher than the pepper yield of a check variety of the same type; (ii) less than 0.4% of fruits remaining on the plant post mechanical harvest; (iii) a width to height ratio greater than 0.9 at maturity; (iv) greater than 3 pre-bifurcation branches at maturity; (v) greater than 80% matured fruits at harvest time; (vi) a canopy angle greater than 65° at maturity; (vii) a fruit concentration greater than 0.15 lbs/inch.

In some embodiments the machine harvestable pepper has at least 4, 5, 6, or all the phenotypic traits i-vii.

In some embodiments the machine harvestable pepper has all the phenotypic traits i-vii.

In other embodiments the machine harvestable pepper plant of claim with determinate growth habit further comprises: (i) a pepper yield at least 19% higher than the pepper yield of a check variety of the same type; (ii) greater than 3 pre-bifurcation branches at maturity; and (iii) a canopy angle greater than 65° at maturity.

In some embodiments, the present invention teaches a machine harvestable pepper plant, wherein said plant has determinate growth habit and at least three of the further phenotypic traits including: (i) a pepper yield at least 19% higher than the pepper yield of a check variety of the same type; (ii) less than 0.4% of fruits remaining on the plant post mechanical harvest; (iii) a width to height ratio greater than 0.9 at maturity; (iv) greater than 3 pre-bifurcation branches at maturity; (v) greater than 80% matured fruits at harvest time; (vi) a canopy angle greater than 65° at maturity; (vii) a fruit concentration greater than 0.15 lbs/inch; further comprising one or more of the following phenotypic traits including: (i) a branching angle greater than 40°; (ii) an internode length of less than 8.5 cm; (iii) a pod detachment force of less than 30 Newtons; (iv) a commercially acceptable fruit weight between 50 g and 80 g; (v) a yield to biomass percentage greater than 75%; (vi) a harvest efficiency in bins of at least 80%; (vii) a total harvesting efficiency of at least 90%; (viii) a high fruit resistance to break (i.e. a percentage of broken fruits <5%); (ix) a commercially acceptable wall thickness between 5 and 8 millimeters; (x) an easy destemming fruit (i.e. a percentage of destemming >50%).

In some embodiments, the machine harvestable pepper plant of the present invention is of the species *Capsicum annuum*.

In some embodiments, the machine harvestable pepper plant of the present invention is a sweet Jalapeño pepper plant.

In some embodiments, the machine harvestable pepper plant of the present invention is a hot Jalapeño pepper plant.

In some embodiments, the invention includes a fruit of the machine harvestable pepper of the present invention.

In some embodiments, the invention includes a seed of the machine harvestable pepper of the present invention.

In some embodiments, the machine harvestable pepper plant is the pepper plant, for which a representative sample of a seed producing such plants been deposited under ATCC Accession Number PTA-121088 or PTA-121087.

In some embodiments, the invention teaches the fruit or seed of the machine harvestable pepper plant is the pepper plant, for which a representative sample of a seed producing such plants been deposited under ATCC Accession Number PTA-121088 or PTA-121087.

In some embodiments, the machine harvestable pepper plant is the pepper plant S5017, or S5082, for which a representative sample of the seed of which has been deposited under ATCC Accession Number PTA-121088, or ATCC Accession Number PTA-121087 respectively.

In some embodiments, the invention teaches the fruit or seed of the machine harvestable pepper plant S5017, or S5082, for which a representative sample of the seed of which has been deposited under ATCC Accession Number PTA-121088 or PTA-121087, or ATCC Accession Number PTA-121088 or PTA-121087 respectively.

In some embodiments the present invention teaches methods of breeding peppers comprising: (i) making a cross between a machine harvestable pepper plant of the present invention, with a second plant to produce an F1 plant; and (ii) harvesting the resulting seed; wherein said seed is capable of germinating.

In some embodiments the invention teaches the pepper plant produced by the breeding method of the present invention.

In some embodiments, the present invention teaches a method of producing pepper fruits, said method comprising: placing a seed from a machine harvestable pepper plant of the present invention in an environment conducive to germination, allowing said seed to germinate into a plant; and allowing said plant to produce pepper fruits.

In some embodiments, the present invention teaches a method of producing pepper fruits, said method comprising: placing a seed from a machine harvestable pepper plant of the present invention in an environment conducive to germination, allowing said seed to germinate into a plant; and allowing said plant to produce pepper fruits.

In some embodiments, the present invention teaches methods of harvesting the machine harvestable pepper plants of the present invention, said method comprising harvesting the fruit of a mature pepper plant using a harvesting machine.

In some embodiments, the harvesting machine of the present invention is a tomato harvesting machine.

In some embodiments, the harvesting machine of the present invention further comprises a mechanical destemmer.

In some embodiments, the plant ideotype according to the invention has a determinate growth habit, and at least a yield 19% higher than the pepper yield of a check variety of the same type, pre-bifurcation branches >3, and a canopy angle >65°. In fact, none of the check varieties have such a combination of phenotypic traits.

In some embodiments the plant ideotype may also have a percentage of fruits intact in the plant <0.4%, a width to height ratio >0.9, a percentage of matured fruits >80%, and a fruit concentration >0.15 lb/inch.

In some embodiments, the plant ideotype of the present invention has the following phenotypic traits: a branching angle >40 degrees, an internode length <8.5 cm, a pod detachment force <30N, a fruit weight from 5 plants >15 lb, a percentage of yield to biomass >75%, a weight of fruits on the ground post mechanical harvest <20lb, a percentage of fruits on the ground post mechanical harvest <9%, a percentage of broken fruits during mechanical harvest <5%, a wall thickness comprising between 5 mm to 6.5 mm, a percentage of destemming >50%, a percentage of harvest efficiency in bins >80%, and percentage of total harvest efficiency >90%.

DETAILED DESCRIPTION

Figure 1:
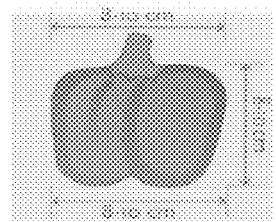
FIG. 1 provides a schematic of the blocky type, half long and ¾ long fruit types of pepper.
Figure 1:
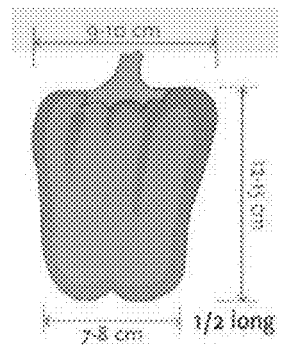
Figure 1:
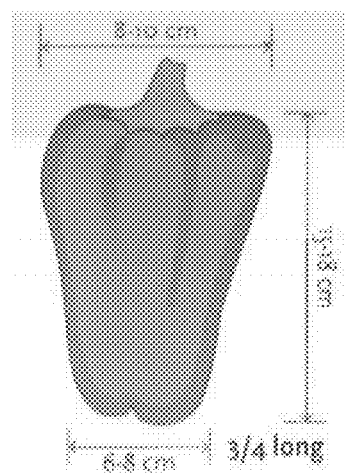

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom).

As used herein, the term "plant part" refers to any part of a plant including but not limited to the shoot, root, stem, seeds, fruits, stipules, leaves, petals, flowers, ovules, bracts, branches, petioles, internodes, bark, pubescence, tillers, rhizomes, fronds, blades, pollen, stamen, rootstock, scion and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus. As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (TO) plant regenerated from material of that line; (b) has a pedigree comprised of a TO plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present invention relates to QTLs, i.e. genomic regions that may comprise one or more genes or regulatory sequences, it is in some instances more accurate to refer to "haplotype" (i.e. an allele of a chromosomal segment) in stead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "mass selection" refers to a form of selection in which individual plants are selected and the next generation propagated from the aggregate of their seeds. More details of mass selection are described herein in the specification.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "self-crossing", "self pollinated" or "self-pollination" means the pollen of one flower on one plant is applied (artificially or naturally) to the ovule (stigma) of the same or a different flower on the same plant.

As used herein, the term "shoulder" refers to the portion of the pepper fruit where the area around the stem begins to drop-off to the sides of the fruit. It is the area forming the angle between the top of the fruit and the sides of the fruit.

As used herein, the terms "Quantitative Trait Loci" and "QTL" are used herein in their art-recognized meaning. A QTL may for instance comprise one or more genes of which the products confer the genetic resistance. Alternatively, a QTL may for instance comprise regulatory genes or sequences of which the products influence the expression of genes on other loci in the genome of the plant thereby conferring the resistance. The QTLs of the present invention may be defined by indicating their genetic location in the genome of the respective pathogen-resistant accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 November 11; 23(21): 4407-4414).

Capsicum

The term pepper as used in agriculture may refer to quite different plant species. For example, some plants in the genera Piper, *Capsicum, Pimenta, Zanthoxylum, Schinus*, and several other species are called pepper. As used herein, the term pepper mainly refers to a plant species in the *Capsicum* genus, unless specified otherwise.

*Capsicum* is a genus of flowering plants in the Solanaceae family. Its species are native to the Americas, where they have been cultivated for thousands of years by the people of the tropical Americas, and are now cultivated worldwide. Some of the members of *Capsicum* are used as spices, vegetables, and medicines. The fruit of *Capsicum* plants have a variety of names depending on geographic location and fruit shape or type. They are commonly called chilli pepper, red or green pepper, or sweet pepper in Britain, and typically called just *capsicum* in Australia, New Zealand, and Indian English. The large mild form is called bell pepper in the U.S. and Canada. They are called paprika in some other countries (although, somewhat confusingly, paprika can also refer to the powdered spice made from various *capsicum* fruit).

The fruit of most species of *Capsicum* contain capsaicin (methyl vanillyl nonenamide), a lipophilic chemical that can produce a strong burning sensation in the mouth of the unaccustomed eater. The secretion of capsaicin protects the fruit from consumption by mammals while the bright colors attract birds that will disperse the seeds.

Capsaicin is present in largest quantities in the placental tissue (which holds the seeds), the internal membranes and, to a lesser extent, the other fleshy parts of the fruits of plants in the genus *Capsicum*. The seeds themselves do not produce any capsaicin, although the highest concentration of capsaicin can be found in the white pith around the seeds.

The amount of capsaicin in Capsicums is highly variable and dependent on genetics, giving almost all types of Capsicums varied amounts of perceived heat.

Chili peppers are of great importance in Native American medicine, and capsaicin is used in modern medicine— mainly in topical medications—as a circulatory stimulant and analgesic. In more recent times, an aerosol extract of capsaicin, usually known as *capsicum* or pepper spray, has become widely used by police forces as a non-lethal means of incapacitating a person, and in a more widely dispersed form for riot control, or by individuals for personal defense. Although black pepper and Sichuan pepper cause similar burning sensations, they are caused by different substances—piperine and hydroxy-alpha sanshool, respectively.

Non-limiting exemplary *Capsicum* species include, *C. annuum*, *C. frutescens*, *C. chinense*, *C. pendulum*, *C. pubescens*, *C. minimum*, *C. baccatum*, *C. abbreviatum*, *C. anomalum*, *C. breviflorum*, *C. buforum*, *C. brasilianum*, *C. campylopodium*, *C. cardenasii*, *C. chacoense*, *C. ciliare*, *C. ciliatum*, *C. chlorocladium*, *C. coccineum*, *C. cordiforme*, *C. cornutum*, *C. dimorphum*, *C. dusenii*, *C. exile*, *C. eximium*, *C. fasciculatum*, *C. fastigiatum*, *C. flexuosum*, *C. galapagoense*, *C. geminifolium*, *C. hookerianum*, *C. lanceolatum*, *C. leptopodum*, *C. luteum*, *C. microcarpum*, *C. minutiflorum*, *C. mirabile*, *C. parvifolium*, *C. praetermissum*, *C. schottianum*, *C. scolnikianum*, *C. stramonifolium*, *C. tetragonum*, *C. tovarii*, *C. villosum*, and *C. violaceum*. More *Capsicum* species are described in Heiser and Smith (The cultivated *Capsicum* peppers. Econ Bot 7:214-227), Pickersgill (1988, The genus *Capsicum*: a multidisciplinary approach to the taxonomy of cultivated and wild plants. Biologisches Zentralblatt 107:381-389), De (*Capsicum*: the genus *Capsicum*, Volume 33 of Medicinal and aromatic plants, Publisher CRC Press, 2003, ISBN 0415299918, 9780415299916), Bosland and Votava (Peppers: vegetable and spice capsicums, Issue 12 of Crop production science in horticulture, Publisher CABI, 2000, ISBN 0851993354, 9780851993355), and Andrews (Peppers: the domesticated Capsicums, Publisher University of Texas Press, 1995, ISBN 0292704674, 9780292704671).

*Capsicum* species have been characterized based on morphology, isozyme analysis, cytology, hybridization, restriction fragment length polymorphism (RFLP), amplified fragment length polymorphism (AFLP), random amplified polymorphic DNA (RAPD), sequence specific amplification polymorphism (S-SAP), simple sequence repeat length polymorphism (SSRLP), inter-simple sequence repeats (ISSR), cleaved amplified polymorphic sequence (CAPS), and direct or directed amplification of minisatellite region DNA amplified using the polymerase chain reaction (DAMD-PCR), for the identification of genotypes or accessions at the taxonomic level, assessment of the relative diversity or similarity within and between species, and selection of diverse accessions with desirable traits for breeding purposes (Eshbaugh 1993; Prince et al. 1992; Rodriguez et al. 1999; Lefebvre et al. 2001; Adetula 2006; Guzman et al. 2005; Ince et al. 2009).

Most *Capsicum* species are diploid (2n=2x=24), but there are a few species for which the genome is 2n=2x=32. *Capsicum* has a large genome, with the DNA content ranging from 7.65 pg/nucleus in *C. annuum* to 9.72 pg/nucleus in *C. pubescens*, and with a general mean of 8.42 pg/nucleus. *Capsicum* genes have been studied for almost a century since 1912, and a list of genes and related traits are described by Wang (2006, The Genes of *Capsicum*, HortScience 41(5) 1169-1187), which is incorporated by reference in its entirety. These genes include, but are not limited to, genes determining morphological traits (such as plant height, flaccid phenotypes, branching habits, fasciculation, leaf shape, color of plant parts, variegated seedlings, flowers, fruit shapes, immature fruit colors, mature fruit colors, transition of fruit colors), genes determining physiological traits (such as pungency, beta-carotene contents, soft flesh and deciduous fruits), genes determining sterility traits (such as genic male sterility, cytoplasmic male sterility, functional male sterility, female sterility), and genes determining resistance to diseases, nematodes, and herbicides (such as resistance to tobacco mosaic virus, resistance to cucumber mosaic virus, resistance to potyvirus, resistance to tomato spotted wilt tospovirus, resistance to bacterial leaf spot, resistance to *phytophthora*, resistance to anthracnose, resistance to *Ralstonia solanacearum*, resistance to powdery mildew, resistance to root knot nematodes, and bentazon herbicide tolerance).

Six genes have been identified to affect the characteristics of fruit shapes. Deshpande (1933, Studies in Indian chillies. 3. The inheritance of some characters in *Capsicum annuum* L. Indian Jour. Agr. Sci. 3:219-300) described the dominant gene P for pointed fruit apex, the recessive gene fb for fruit base nonbulging, and the gene ce for calyx enclosed around fruit base (Daskalov and Poulos, 1994, Updated *Capsicum* gene list, *Capsicum* Eggplant Nswl. 13:16-26). The round fruit shape is controlled by the major dominant gene O and other modifiers (Peterson, 1959, Linkage of fruit shape and color genes in *Capsicum*, Genetics, 44:407-419), and recent molecular mapping studies confirm the existence of the major genes that control this trait (Ben Chaim et al., 2001, QTL mapping of fruit-related traits in pepper (*Capsicum annuum*). Theor. Appl. Genet. 102:1016-1028; Ben Chaim et al., 2003, Linkage of the A locus for the presence of anthocyanin and fs10.1, a major fruit-shape QTL in pepper. Theor. Appl. Genet., 106:889-894; and Rao and Paran, 2003, Polygalacturonase: A candidate gene for the soft flesh and deciduous fruit mutation in *Capsicum*, Plant Mol. Biol. 51:135-141). Upright fruit orientation is controlled by two recessive genes (up-1 and up-2) that show specific dominant and recessive epistasis respectively (Gopalakrishnan et al., 1990, Inheritance of clusterness and fruit orientation in chili (*Capsicum annuum* L.) Indian J. Genetics 49:219-222; Lippert et al., 1965, Gene list for the pepper. J. Hered. 56:30-34). Csillery (1983, New *Capsicum* mutants found on seedling, growth type, leaf, flower and fruit. Proc. 5$^{th}$ Eucarpia Meeting of *Capsicum* and Eggplant Working Group, 4-7 Jul. 1983, Plovdiv. 127-130) identified the recessive gene cy, responsible for the exocarp covered with transversally oriented, small suberized cracks at full fruit maturity. Ishikawa and coworkers (1998, Inheritance of the fruit shape at the apex and the peduncle attachment of pepper, *Capsicum* Eggplant Nswl. 17:30-33) reported the dominant Ap and Ped genes to condition the pointed shape of the fruit apex, and the acute shape of the fruit pedicle attachment respectively. The allelism between Ap and P is unknown. Each of the publications mentioned above is incorporated by reference in its entirety.

Enzymatic studies of *Capsicum* (Jensen et al., 1979; McLeod et al, 1979a, 1979b, 1982, 1983) have demonstrated that *Capsicum* species can be grouped into three taxonomic categories (*Capsicum annuum* complex, *Capsicum baccatum* complex, and *Capsicum eximium* complex) that somewhat agreed with groupings based on flower color. Hybrid analyses have been used extensively to resolve species relationships in *Capsicum* (Heiser and Smith 1948, 1953, 1958; Smith and Heiser 1951, 1957; Emboden 1961; Lippert et al. 1966; Eshbaugh 1970, 1976; Peckersgill 1971; Eshbaugh et al. 1983, each of which is incorporated by reference in its entirety). To determine the viability of hybrids between various species of *Capsicum*, pollen staining and F1 seed germination studies were used. Interspecific hybridization among *Capsicum* species are also discussed by Bosland and Votava (Peppers: vegetable and spice capsicums, Issue 12 of Crop production science in horticulture, Publisher: CABI, 2000, ISBN 0851993354, 9780851993355), which is incorporated by reference in its entirety.

*Capsicum annuum*

*Capsicum annuum* is a domesticated species of the plant genus *Capsicum* native to South America and it is now cultivated worldwide. Despite being a single species, the *Capsicum annuum* has many forms, with a variety of names, even in the same language. In American English it is commonly known as the chili pepper, although not all varieties would be recognized by most speakers under this name. In British English, the sweet varieties are called peppers and the hot varieties are called chillies, whereas in Australian English the name *capsicum* is commonly used for bell peppers exclusively and chilli is often used to encompass the hotter varieties. Its forms are varied, from large to small, sweet to sour, very hot to bland.

The plant is an herbaceous annual, with a densely branched stem. The plant reaches 0.5-1.5 m (20-60 in). Single white flowers bear the fruit which is green when unripe, changing principally to red, although some varieties may ripen to brown or purple. While the species can tolerate most climates, they are especially productive in warm and dry climates.

Non-limiting exemplary *Capsicum annuum* types and varieties include, Aleppo, Anaheim, Bell, Ancho (a dried version of Poblano), Cascabel, Cayenne, Cherry, Chilaca, Chiltepin, Cubanelle, De arbol, Fresno, Guajillo, Guntur, Sannam, Hungarian wax, Italian sweet pepper, Jalapeño (hot Jalapeño and sweet Jalapeño), Japanese, Mirasol, Macho, New Mexico, Pepperoncini, Pequin pepper, Poblano, Puya, Serrano, Super Chili, and Tien Tsin.

Bell Pepper

Bell pepper or sweet pepper or sweet bell pepper is a cultivar group of the species *Capsicum annuum*. Cultivars of the plant produce fruits in different colors, for example, green, red, yellow, orange, white, purple, and rainbow, depending on when they are harvested and the specific cultivar. The term "bell pepper" is often used for any of the large bell shaped *capsicum* fruits, regardless of their color. As used herein, the phrase "bell pepper" is equivalent to "blocky type pepper" or "blocky shape pepper", as this term is understood by those skilled in the art of pepper breeding and pepper production. The fruit is also frequently consumed in its unripe form, when the fruit is still green.

In the United States and Canada, in addition to the terms "bell pepper" and "sweet pepper," the fruit is often referred to simply as a "pepper" or referred to by color (e.g. "red bell", "red pepper", "green pepper", "yellow pepper"), although the more specific term "bell pepper" is understood in most regions. In parts of Indiana, Ohio, and Pennsylvania, the fruit is called a "mango". The origin of this use is in the use of the term "mango" or "mangoed" to refer to pickled fruits. At a certain time, mangoes were available in the United States only in pickled form. Later, it became common in these regions to use bell peppers in pickled form, thus the term "mangoed peppers" or "mango peppers" later shortened to "mangoes."

Green peppers are less sweet and slightly bitter than red, yellow or orange peppers. The taste of ripe peppers can also vary with growing conditions and post-harvest storage treatment; the sweetest are fruit allowed to ripen fully on the plant in full sunshine, while fruit harvested green and after-ripened in storage are less sweet. Compared to green peppers, red peppers have more vitamins and nutrients and contain the antioxidant lycopene. The level of carotene, another antioxidant, is nine times higher in red peppers. Red peppers also have twice the vitamin C content of green peppers. Orange bell peppers (or paprikas) contain even more vitamin C and significantly more vitamin A. Orange bell peppers are both juicy and sweet, and because they contain less than half the calories of an orange, orange bell peppers are pre-eminently appropriate as a refreshing, low-calorie food, both raw and prepared in any dish. They can be eaten raw without having indigestion later.

*Capsicum* Plants for Machine Harvesting and Other Desirable Agronomic Traits

The present invention provides *Capsicum* plants which are machine harvestable. In one embodiment, said *Capsicum* plants are *Capsicum annuum* plants. In some other embodiments, said *Capsicum* plant is derived a progeny produced by a cross between a first *Capsicum* parent and a second *Capsicum* parent, wherein at least one of the parent is a *Capsicum annuum* plant. In some embodiments, the other *Capsicum* parent is a *Capsicum* plant selected from the group consisting of *C. frutescens, C. chinense, C. pendulum, C. pubescens, C. minimum, C. baccatum, C. abbreviatum, C. anomalum, C. breviflorum, C. buforum, C. brasilianum, C. campylopodium, C. cardenasii, C. chacoense, C. ciliare, C. ciliatum, C. chlorocladium, C. coccineum, C. cordiforme, C. cornutum, C. dimorphum, C. dusenii, C. exile, C. eximium, C. fasciculatum, C. fastigiatum, C. flexuosum, C. galapagoense, C. geminifolum, C. hookerianum, C. lanceolatum, C. leptopodum, C. luteum, C. microcarpum, C. minutiflorum, C. mirabile, C. parvifolium, C. praetermissum, C. schottianum, C. scolnikianum, C. stramonifolium, C. tetragonum, C. tovarii, C. villosum, C. violaceum*, and *Capsicum* species derived from thereof. Cross compatibility between *Capsicum* species are described herein in the specification.

In one embodiment, the machine harvestable pepper of the present invention have additional agronomic traits related to fruit which are selected from the group consisting of fruit shape, fruit weight, ripening date, fruit diameter, fruit length, pericarp thickness, soluble solids concentration, pedicel diameter, pedicel length, seed weight, firmness, and fruit color. In one embodiment, said fruit shape traits are related to blocky type fruit (bell pepper) or rectangular ¾ long types or half long fruit type. Such fruit shapes are well-known to those skilled in the art of pepper breeding. Non-limiting examples of blocky type pepper, half long type pepper, and ¾ long type pepper are shown in FIG. 1. As used herein, blocky type pepper refers to a pepper wherein the length of the fruit is about the same as the width of the fruit. For example, the length of the fruit is about 0.8, about 0.9, about 1.0, about 1.1, or less than 1.2 of the width of the fruit. As used herein, half long type pepper refers to a pepper wherein the length of the fruit is about 1.2 to about 1.5 of the width of the fruit. As used herein, ¾ long type pepper, often known as lamuyo refers to a pepper wherein the length of the fruit is more than about 1.5 of the width of the fruit. In further embodiments, said fruit traits are determined by the genes and/or QTLs described herein, e.g., those described in Wang et al., 2006, Ben Chaim 2001, Ben Chaim et al., 2003a, 2003b, Rao et al., 2003, Bachi et al. 2009, and Zygier et al., 2005. In some embodiments, said fruit traits are fruit shape ("fs") and/or fruit weight ("fw").

In further embodiments, the *Capsicum* plants of the present invention comprise one or more other agronomic traits. For example, such traits can be morphological traits (such as plant height, flaccid phenotypes, branching habits, fasciculation, leaf shape, color of plant parts, variegated seedlings, flowers, immature fruit colors, mature fruit colors, transition of fruit colors), physiological traits (such as pungency, beta-carotene contents, soft flesh and deciduous fruits), sterility traits (such as genic male sterility, cytoplasmic male sterility, functional male sterility, female sterility), and resistance to diseases, nematodes, and herbicides (such as resistance to bacterial, viral and fungal diseases, e.g., resistance to tobacco mosaic virus, resistance to cucumber mosaic virus, resistance to potyvirus, resistance to tomato spotted wilt tospovirus, resistance to bacterial leaf spot, resistance to *phytophthora*, resistance to anthracnose, resistance to *Ralstonia solanacearum*, resistance to powdery mildew, resistance to root knot nematodes, and bentazon herbicide tolerance).

The present invention also provides a genetically related *Capsicum* plant population (progeny) derived from the *Capsicum* plants described herein. Such genetically related *Capsicum* plant population can be produced through either natural or artificial process, sexually or asexually, e.g., by cutting, grafting, apomixis, layering, division, budding, grafting or tissue culture.

The present invention also provides a seed, a fruit, a plant population, a plant, a plant part, a plant cell and/or a plant tissue culture derived from the plants of the present invention. In one embodiment, the regenerable cells are derived from embryos, protoplasts, meristematic cells, callus, pollen, leaves, anthers, stems, petioles, roots, root tips, fruits, seeds, flowers, cotyledons, or hypocotyls.

Modern plant tissue culture is performed under aseptic conditions under filtered air. Living plant materials from the environment are naturally contaminated on their surfaces (and sometimes interiors) with microorganisms, so surface sterilization of starting materials (explants) in chemical solutions (usually alcohol or bleach) is required. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar.

The composition of the medium, particularly the plant hormones and the nitrogen source (nitrate versus ammonium salts or amino acids) have profound effects on the morphology of the tissues that grow from the initial explant. For example, an excess of auxin will often result in a proliferation of roots, while an excess of cytokinin may yield shoots. A balance of both auxin and cytokinin will often produce an unorganized growth of cells, or callus, but the morphology of the outgrowth will depend on the plant species as well as the medium composition. As cultures grow, pieces are typically sliced off and transferred to new media (subculture) to allow for growth or to alter the morphology of the culture. The skill and experience of the tissue culturist are important in judging which pieces to culture and which to discard. As shoots emerge from a culture, they may be sliced off and rooted with auxin to produce plantlets which, when mature, can be transferred to potting soil for further growth in the greenhouse as normal plants.

The tissue obtained from the plant to culture is called an explant. Based on work with certain model systems, particularly tobacco, it has often been claimed that a totipotent explant can be grown from any part of the plant. However, this concept has been vitiated in practice. In many species explants of various organs vary in their rates of growth and regeneration, while some do not grow at all. The choice of explant material also determines if the plantlets developed via tissue culture are haploid or diploid. Also the risk of microbial contamination is increased with inappropriate explants. Thus it is very important that an appropriate choice of explant be made prior to tissue culture.

The specific differences in the regeneration potential of different organs and explants have various explanations. The significant factors include differences in the stage of the cells in the cell cycle, the availability of or ability to transport endogenous growth regulators, and the metabolic capabilities of the cells. The most commonly used tissue explants are the meristematic ends of the plants like the stem tip, auxiliary bud tip and root tip. These tissues have high rates of cell division and either concentrate or produce required growth regulating substances including auxins and cytokinins. Some explants, like the root tip, are hard to isolate and are contaminated with soil microflora that become problematic during the tissue culture process. Certain soil microflora can form tight associations with the root systems, or even grow within the root. Soil particles bound to roots are difficult to remove without injury to the roots that then allows microbial attack. These associated microfloras will generally overgrow the tissue culture medium before there is significant growth of plant tissue. Aerial (above soil) explants are also rich in undesirable microflora. However, they are more easily removed from the explant by gentle rinsing, and the remainder usually can be killed by surface sterilization. Most of the surface microflora does not form tight associations with the plant tissue. Such associations can usually be found by visual inspection as a mosaic, de-colorization or localized necrosis on the surface of the explant.

An alternative for obtaining uncontaminated explants is to take explants from seedlings which are aseptically grown from surface-sterilized seeds. The hard surface of the seed is less permeable to penetration of harsh surface sterilizing agents, such as hypochlorite, so the acceptable conditions of sterilization used for seeds can be much more stringent than for vegetative tissues.

Tissue cultured plants are clones, if the original mother plant used to produce the first explants is susceptible to a pathogen or environmental condition, the entire crop would be susceptible to the same problem, and conversely any positive traits would remain within the line also. Plant tissue culture is used widely in plant science; it also has a number of commercial applications. Applications include:
1. Micropropagation is widely used in forestry and in floriculture. Micropropagation can also be used to conserve rare or endangered plant species.
2. A plant breeder may use tissue culture to screen cells rather than plants for advantageous characters, e.g. pathogen resistance/tolerance.
3. Large-scale growth of plant cells in liquid culture inside bioreactors as a source of secondary products, like recombinant proteins used as biopharmaceuticals.
4. To cross distantly related species by protoplast fusion and regeneration of the novel hybrid.
5. To cross-pollinate distantly related species and then tissue culture the resulting embryo which would otherwise normally die (Embryo Rescue).
6. For production of doubled monoploid (dihaploid) plants from haploid cultures to achieve homozygous lines more rapidly in breeding programs, usually by treatment with colchicine which causes doubling of the chromosome number.
7. As a tissue for transformation, followed by either short-term testing of genetic constructs or regeneration of transgenic plants.

8. Certain techniques such as meristem tip culture can be used to produce clean plant material from infected stock, such as potatoes and many species of soft fruit.
9. Micropropagation using meristem and shoot culture to produce large numbers of identical individuals.

Non-limiting exemplary tissue culture methods for *Capsicum* plants have been described by Arous et al., 2001, Sharma, 2007, Agrawal et al., 1989, Harini and Sita, 1993, and Kothari et al., 2010, each of which is incorporated by reference in its entirety.

The present invention also provides a cutting, a rootstock, a scion, or an explant from the *Capsicum* plants as described above for grafting.

Grafting is a method of asexual plant propagation widely used in agriculture and horticulture where the tissues of one plant are encouraged to fuse with those of another. It is most commonly used for the propagation of trees and shrubs grown commercially. In most cases, one plant is selected for its roots, and this is called the stock or rootstock. The other plant is selected for its stems, leaves, flowers, or fruits and is called the scion. The scion contains the desired genes to be duplicated in future production by the stock/scion plant. In stem grafting, a common grafting method, a shoot of a selected, desired plant cultivar is grafted onto the stock of another type. In another common form called budding, a dormant side bud is grafted on the stem of another stock plant, and when it has fused successfully, it is encouraged to grow by cutting out the stem above the new bud.

For successful grafting to take place, the vascular cambium tissues of the stock and scion plants must be placed in contact with each other. Both tissues must be kept alive until the graft has taken, usually a period of a few weeks. Successful grafting only requires that a vascular connection takes place between the two tissues. A physical weak point often still occurs at the graft, because the structural tissue of the two distinct plants, such as wood, may not fuse.

Exemplary grafting techniques include, approach grafting, budding grafting (patch budding, chip budding, T-budding), cleft grafting, side grafting, whip grafting, stub grafting, awl grafting, veneer grafting, bark grafting, tongue grafting, et al. A detailed grafting method for *Capsicum* species is described by Toth et al., Kokalis-Burelle et al., 2009, and DeWitt and Bosland, 2009, each of which is incorporated by reference in its entirety.

The plants of the present invention can be used for many purposes. In one embodiment, a plant of the present invention is used as a donor plant of genetic material which can be transferred to a recipient plant to produce a plant with desired agronomic traits which has the machine harvestable traits of the present invention. Any suitable method known in the art can be applied to transfer genetic material from a donor plant to a recipient plant. In most cases, such genetic material is genomic material.

In one embodiment, the whole genome of the machine harvestable plants of the present invention is transferred into a recipient plant. This can be done by crossing the plants to a recipient plant to create a F1 plant. The F1 plant can be further selfed and selected for one, two, three, four, or more generations. Selection pressures for certain desirable traits includes but are not limited to a resistance test, molecular marker selection, agronomic traits phenotype selection, or a combination thereof.

In some embodiments, the recipient plant is a *Capsicum annum* plant, or any other *Capsicum* plants that can hybridize with the plants with the machine harvestable traits of the present invention.

In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, increased food production, improved food quality, decrease in cracking, quicker color change when the fruit matures etc. Additional examples of agronomically important traits includes pest resistance, vigor, development time (time to harvest), enhanced nutrient content, novel growth patterns, flavors or colors, salt, heat, drought and cold tolerance, and the like.

Other agronomically important traits include resistance to biotic and/or abiotic stresses. As used herein, the phrase "biotic stress" or "biotic pressure" refers to a situation where damage is done to plants by other living organisms, such as bacteria, viruses, fungi, parasites, insects, weeds, animals and human. As used herein, the phrase "abiotic stress" or "abiotic pressure" refers to the negative impact of non-living factors on plants in a specific environment. The non-living variable must influence the environment beyond its normal range of variation to adversely affect the population performance or individual physiology of plants in a significant way. Non-limiting examples of stressors are high winds, extreme temperatures, drought, flood, and other natural disasters, such as tornados and wildfires.

A list of popular North America *Capsicum* cultivars with various agronomically important traits are well known to those skilled in the art and can also be found in the Vegetable Cultivar Breeding database of North Carolina State University (Bosland, Department of Agronomy and Horticulture, New Mexico State University, Vegetable Cultivar Descriptions for North America, Pepper, Retrieved on Jun. 18, 2010, incorporated by reference in its entirety). More *capsicum* cultivars can be found in the Pepper Database of European Cooperative Program for Plant Genetic Resources (ECPGR).

In one embodiment, the recipient plants and/or lines have one or more preferred traits related to resistance/tolerance to pathogens, such as resistance to pests (e.g., *thrips*, aphids, caterpillars, and whiteflies), fungus (e.g., *Pythium, Rhizoctonia, Leveillula, Verticillium* wilt (*Verticillium dahliae*), *Phytophthora* (*Phytophthora capsici*), Southern blight (*Sclerotium rolfsii*), Ripe rot (*Vermicularia capsici*), Cercospora leaf spot (*Cercospora capsici*), Anthracnose (*Gleosporium piperatum*)), bacteria (e.g., *Xanthomonas vesicatoria, Xanthomonas campestris*,), viruses (e.g., Cucumber mosaic virus (CMV), Tobacco mosaic virus (TMV), Potato virus Y (PVY), Tobacco etch virus (TEV), Pepper mottle virus (PeMV), Tomato spotted wilt virus (TSWV), Tobacco mild virus (TOMV), Pepper mild mottle virus (PMMoV) and nematodes (e.g., root-knot nematode).

Machine Harvestable Traits

Figure 2:
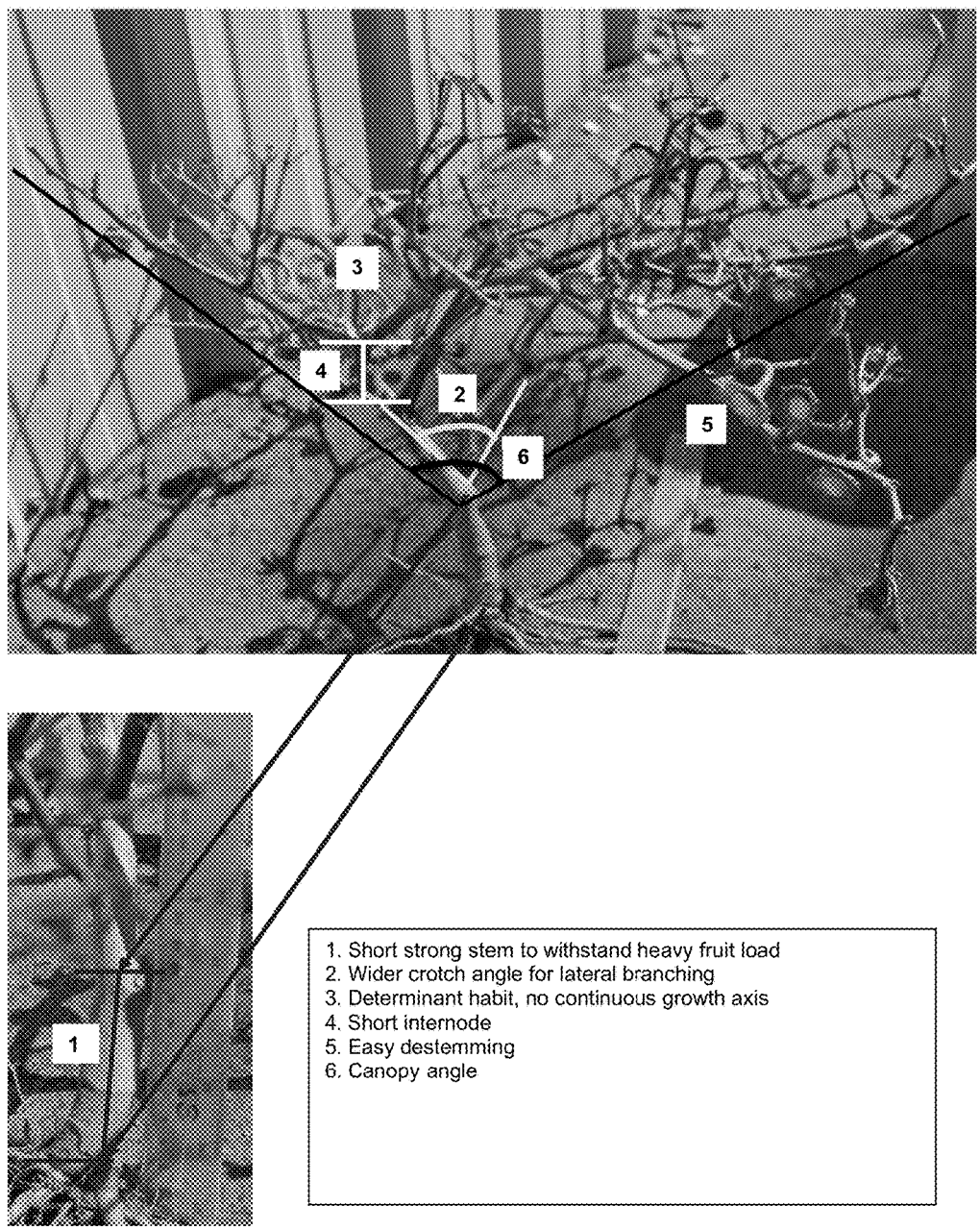
FIG. 2 provides a photograph of a representative pepper plant of 'S5017' with diagrams of some phenotypes taught by the present invention including canopy angle, short strong stem, wider crotch angle for lateral branching, short internodes, easy destemming, and determinate plant growth.

In some embodiments, the present invention teaches traits that are important for machine harvesting pepper plants. In some embodiments, the pepper plant according to the invention has a determinate growth habit. In some embodiments, the canopy angle of the pepper plant is important for the plant's suitability for machine harvesting (FIG. 2). In some embodiments, the machine harvestable pepper plants of the present invention have a canopy angle that is greater than 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 820, 83° 84° 85° 86° 87° 88° 89° 90° 91° 92° 93° 94° 95° 96° 97° 98° 99° 100° 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, 150°, 151°, 152°, 153°, 154°, 155°, 156°, 157°, 158°, 159°, 160°, 161°, 162°, 163°, 164°, 165°, 166°, 167°, 168°, 169°, 170°, 171°, 172°, 173°, 174°, 175°, 176°, 177°, 178°, 179°, or 180° at maturity. In other embodiments the canopy angle of the machine harvestable pepper plants of the present invention is between 65°- and 100° at maturity.

In some embodiments, the machine harvestable pepper plants of the present invention have a canopy angle that is 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 175%, 200%, 225%, 250%, 275%, 300%, 325%, 350%, 375%, 400%, 425%, 450%, 475%, or 500% greater than the canopy angle of a check variety grown under similar field conditions.

In some embodiments the number of pre-bifurcation branches on the pepper plants is an important trait for their suitability for machine harvesting. In some embodiments the pre-bifurcation branches in the pepper plants of the present invention increase the fruit concentration to achieve higher yields and provide branching structure better suited for machine harvesting. In some embodiments the machine harvestable peppers of the present invention comprise at least 2, 3, 4, 5, 6, 7, 8, 9, or 10 pre-bifurcation branches at maturity. In some embodiments the machine harvestable pepper plants have between 3 and 10 pre-bifurcation branches at maturity. In some embodiments the machine harvestable pepper plants have between 3 and 5 pre-bifurcation branches at maturity.

In some embodiments, the machine harvestable peppers plants of the present invention have a fruit concentration that is greater than 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, or 0.75 pounds of fruit per inch (lbs/inch) at maturity.

In some embodiments, the machine harvestable pepper plants of the present invention have high yield. In some embodiments, the machine harvestable peppers of the present invention have a pepper fruit yield greater than 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, 60.5, 61, 61.5, 62, 62.5, 63, 63.5, 64, 64.5, 65, 70, 75, 80, 85, 90, or 100 tons per acre (t/a). In some embodiments, the machine harvestable pepper plants of the present invention have a pepper yield between 30 t/a and 60 t/a.

In some embodiments, the machine harvestable pepper plants of the present invention have a pepper fruit yield that is 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 175%, 200%, 225%, 250%, 275%, 300%, 325%, 350%, 375%, 400%, 425%, 450%, 475%, or 500% greater than the yield of a check variety grown under similar field conditions.

In some embodiments, the width to height ratio of the machine harvestable pepper plants of the present invention is bred for optimal suitability for machine harvesting. In some embodiments the width to height ratio of the machine harvestable peppers of the present invention is greater than 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, or 2.0, at maturity.

In some embodiments, the machine harvestable pepper plants of the present invention have a total harvest efficiency of at least 90%, 91%, 92%, 93%, 94%, 95%, 96%, 97%, 98%, 99%, or 100% using a mechanical harvesting method.

In some embodiments, the machine harvestable pepper plants of the present invention have harvest efficiency in bins of at least 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% using a mechanical harvesting method.

In some embodiments, the machine harvestable pepper plants of the present invention have at least 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of its fruits mature at the time of harvesting.

In some embodiments, the machine harvestable pepper plants of the present invention have a wide branching angle. In some embodiments, the branching angle of a pepper plant is defined as an average angle measurement between any two branches. In some embodiments the branching angle of a pepper plant is an average of at least 5 branches from 5 different randomly chosen plants. In some embodiments the machine harvestable pepper plants of the present invention have a branching angle wider than 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, 90°, 91°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, or 150°.

In some embodiments the machine harvestable pepper plants of the present invention have a pod detachment force less than 1N, 2N, 3N, 4N, 5N, 6N, 7N, 8N, 9N, 10N, 11N, 12N, 13N, 14N, 15N, 16N, 17N, 18N, 19N, 20N, 21N, 22N, 23N, 24N, 25N, 26N, 27N, 28N, 29N, 30N, 31N, 32N, 33N, 34N, 35N, 36N, 37N, 38N, 39N, 40N, 41N, 42N, 43N, 44N, 45N, 46N, 47N, 48N, 49N, or 50 Newtons (N) at maturity.

In some embodiments the machine harvestable pepper plants of the present invention have a pod detachment force between 15 and 30N.

In some embodiments the machine harvestable pepper plants of the present invention have a commercially acceptable fruit weight. In some embodiments machine harvestable peppers of the present invention have an average fruit weight greater than 40 g, 41 g, 42 g, 43 g, 44 g, 45 g, 46 g, 47 g, 48 g, 49 g, 50 g, 51 g, 52 g, 53 g, 54 g, 55 g, 56 g, 57 g, 58 g, 59 g, 60 g, 61 g, 62 g, 63 g, 64 g, 65 g, 66 g, 67 g, 68 g, 69 g, 70 g, 71 g, 72 g, 73 g, 74 g, 75 g, 76 g, 77 g, 78 g, 79 g, 80 g, 81 g, 82 g, 83 g, 84 g, 85 g, 86 g, 87 g, 88 g, 89 g, 90 g, 91 g, 92 g, 93 g, 94 g, 95 g, 96 g, 97 g, 98 g, 99 g, or 100 grams per fruit at maturity.

In some embodiments the machine harvestable pepper plants of the present invention have a fruit weight between 60 and 80 grams at maturity.

In some embodiments the machine harvestable pepper plants of the present invention have a commercially acceptable fruit wall thickness. In some embodiments, commercially acceptable fruit wall thickness is greater than 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, 5.1 mm, 5.2 mm, 5.3 mm, 5.4 mm, 5.5 mm, 5.6 mm, 5.7 mm, 5.8 mm, 5.9 mm, 6.0 mm, 6.1 mm, 6.2 mm, 6.3 mm, 6.4 mm, 6.5 mm, 6.6 mm, 6.7 mm, 6.8 mm, 6.9 mm, 7.0 mm, 7.1 mm, 7.2 mm, 7.3 mm, 7.4 mm, 7.5 mm, 7.6 mm, 7.7 mm, 7.8 mm, 7.9 mm, 8.0 mm, 8.1 mm, 8.2 mm, 8.3 mm, 8.4 mm, 8.5 mm, 8.6 mm, 8.7 mm, 8.8 mm, 8.9 mm, 9.0 mm, 9.1 mm, 9.2 mm, 9.3 mm, 9.4 mm, 9.5 mm, 9.6 mm, 9.7 mm, 9.8 mm, 9.9 mm, or 10.0 millimeters at maturity.

In some embodiments, the machine harvestable pepper plants of the present invention have a fruit wall thickness between 5 and 8 millimeters, and more preferably between 5 and 6.5 millimeters.

In some embodiments the machine harvestable pepper plants of the present invention have a high yield to biomass percent. In some embodiments the machine harvestable peppers of the present invention have a yield to biomass percent greater than 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% at maturity.

In some embodiments the machine harvestable pepper plants of the present invention have shorter internodes than those of a check variety grown under similar field conditions. In some embodiments, the machine harvestable peppers of the present invention have an average internode length less than 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, or 10 centimeters at maturity.

In some embodiments the machine harvestable pepper plants of the present invention have optimal maturity at the time of harvest. In some embodiments the fruits machine harvestable peppers of the present invention have greater than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the fruits mature at the time of harvest.

Methods of producing *Capsicum* Plants with Machine Harvestable Traits and Other Desirable Agronomic Traits Any *Capsicum* plant with the machine harvestable traits of the present invention can be used to produce more *Capsicum* plants that have such machine harvestable traits through plant breeding methods well known to those skilled in the art. The goal in general is to develop new, unique and superior varieties and hybrids. In some embodiments, selection methods, e.g., molecular marker assisted selection, can be combined with breeding methods to accelerate the process.

Choice of breeding or selection methods depends on the mode of plant reproduction, the heritability of the trait(s) being improved, and the type of cultivar used commercially (e.g., F1 hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Non-limiting breeding methods commonly include pedigree selection, modified pedigree selection, mass selection, recurrent selection, and backcross breeding.

The complexity of inheritance influences choice of the breeding method. Backcross breeding is used to transfer one or a few favorable genes for a heritable trait into a desirable cultivar. This approach has been used extensively for breeding disease-resistant cultivars; nevertheless, it is also suitable for the adjustment and selection of morphological characters, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc).

Promising advanced breeding lines are thoroughly tested per se and in hybrid combination and compared to appropriate standards in environments representative of the commercial target area(s) for three years at least. The best lines are candidates for use as parents in new commercial cultivars; those still deficient in a few traits may be used as parents to produce new populations for further selection.

To select plants with desired agronomic traits, an elite control plant can be involved for comparison. Desired agronomic traits, such as fruit weight and fruit shape can be compared among the population under selection and the elite control plant.

In one embodiment, the evaluating step comprises visual observation to determine the severity of the pathogen infection, using a resistance scoring system. The resistance scoring system is well known in the art and is described elsewhere herein.

Breeding Methods

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, Plant Breeding Methodology, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA).

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*, 99:9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding.

The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

Tomato Harvesting Equipment

Tomato harvesting machines have been used in harvesting tomato fruit in the field since at least 1949 (K. Coatney, Mar. 15, 2006, *The machine that revolutionized a harvest*, AgAlert, The Weekly Newspaper for California Agriculture). A number of different types of tomato harvesting equipment are commercially available. See, e.g., tomato harvesting machines available from California Tomato Machinery, Westside Equipment Company, Pomac, and Pik Rite. Examples of tomato harvesting machines are described in U.S. Pat. Nos. 4,232,506; 4,915,671; 5,685,773; 5,911,625; 6,003,293; 6,675,568; 7,051,505; 7,694,502; 7,581,375; and 7,921,628, each of which is incorporated herein in its entirety.

EXAMPLES

Example 1. Pepper Ideotype for Machine Harvesting

We sought to develop a pepper plant ideotype that can be machine harvested on large acreage plantings. We hypothesized that it would be best for pepper growers and commercial pepper harvesters if the plant ideotype could be harvested using currently-available harvesting equipment (e.g., a tomato harvesting machine). By using existing harvesting equipment, we believed the pepper industry could more quickly adopt this new technology without having to incur a huge upfront investment on developing and purchasing a separate harvester for peppers.

Thus, the present invention is based in part on the discovery of the phenotypes and selections that are important for breeding machine harvestable peppers. In some embodiments, the phenotypes taught in the present invention could allow a person of ordinary skill to produce a machine harvestable variety of any pepper species. According to one ideotype of the present invention, the pepper plant ideotype for machine harvesting includes the following combination of phenotypic or morphological characteristics: (1) determinate plant growth habit, (2) high yield, (3) wide canopy angle, (4) increased number of pre-bifurcation branches. In some embodiments, the pepper plant ideotype for machine harvesting according to the present invention further has one or more additional phenotypic or morphological characteristics including: greater than (5) 80% or about 80% matured fruits at harvest time; (6) a canopy angle greater than 65 degrees or about 65 degrees at maturity; (7) a fruit concentration greater than 0.15 lbs/inch or about 0.15 lbs/inch.

The pepper plant ideotype for machine harvesting according to the present invention further has one or more additional phenotypic or morphological characteristics including (8) a wide branching angle, (9) short internodes length, (10) a low pod detachment force, (11) a commercially acceptable fruit weight, (12) a high percentage of yield to biomass, (13) a low weight or percentage of fruits on the ground, (14) a low percentage of fruits in plant after harvest, (15) a high resistance to break, (16) a commercially acceptable wall thickness, (17) an easy fruit destemming, (18) a high percentage of harvest efficiency (in bins and in total, i.e. when fruits on the ground are considered as harvest).

In some embodiments, the pepper plant ideotype for machine harvesting according to the present invention also has one or more the following additional phenotypic or morphological characteristics: (19) a strong stem; (20) a uniform maturity.

Methods of measuring these and other related traits are provided below and in Example 4 and Table 10 of this application. As used herein, the phrase "pod detachment force" refers to the force required to remove a pod from its pedicel. The pepper plant ideotype of the present invention has easy (or low) pod detachment force when compared to the hard or harder (or high/higher) pod detachment force of non-ideotype pepper plants. Fruit detachment force can be measured with an Omega Digital force Gauge (Model DGF51) as mentioned in Walker et al (2004, HortScience 39(3):629-630) and/or based on a subjective score assigned by an individual using physical force to detach the pods.

As used herein, the term "destemming" refers to how easy it is to remove a fruit from its pedicel (i.e., ease to remove the fruits from calyx). The pepper plant ideotype of the present invention has easy or easier (or low/lower) destemming when compared to the hard or harder (or high/higher) destemming of non-ideotype pepper plants. Destemming can be measured by holding a pepper fruit in the palm of the hand and applying force by the thumb at the base of calyx so that the pedicel "pops out" from the fruit. The percent destemming (aka the destemming percentage)=(the number of fruits in which the pedicel pops out divided by the total number of fruits tested for destemming)×100. Thus, if 60 fruits of one pepper type (e.g., a variety, a F2 population, etc.) are tested for destemming and 30 of them pop out using this test, the total percent destemming is 50%.

As used herein, the phrases "resistance to breaking" and "resistance to break" refer to pepper plants having a low frequency of bruised or broken fruits. The pepper plant ideotype of the present invention has high or higher resistance to breaking when compared to the low or lower resistance to breaking of non-ideotype pepper plants. In one embodiment, the ideotype of the present invention has thick-walled fruit which have more or greater resistance to breaking when compared to the lower or lesser resistance to breaking of non-ideotype pepper plants with thinner walled fruit.

As used herein, the phrases "branching angle" or "crotch angle" refer to the angle between a branch of the plant and its sub-branch, or in some instances, to the angle between a stem and the branch arising from the stem. In one embodiment, the ideotype varieties of the present invention have a branching angle which is almost horizontal (i.e., branches are ~90° to the stem). In one embodiment, the ideotype varieties of the present invention have a branching angle between two branches that is between about 60° and about 90°.

In one embodiment, the pepper plant ideotype of the present invention has wide or wider branch angles when compared to the narrow or narrower branch angles of non-ideotype pepper plants. In one embodiment, the ideotype pepper plants of the present invention have a wide or wider crotch angle for lateral branching when compared to the narrow or narrower crotch angle for lateral branching of non-ideotype pepper plants.

As used herein the phrase "concentrated flowering fruit set" refers to plants having synchronous flowering and fruit setting which concentrates the yield into a single harvest amenable to machine picking. In one embodiment, the pepper plant ideotype of the present invention has a more or greater concentrated fruit set when compared to the less or lack of concentrated fruit set for non-ideotype pepper plants.

As used herein, the phrase "uniform maturity" refers to a variety which has a large percentage of the plants producing marketable fruit at the time of harvest. In one embodiment, the pepper plant ideotype of the present invention has less than 18% of its fruits that are immature when 82% are mature. A non-ideotype plant will have 20% or more fruit that are not mature when measured at the same harvest stage. In one embodiment, the pepper plant ideotype of the present invention has a more (or greater) uniform maturity when compared to the less or lack of uniform maturity of non-ideotype pepper plants.

As used herein, the phrase "determinate growth" refers to a variety which has a definite growth: the axis being limited by the development of the terminal flower bud or other reproductive structure does not continue to elongate indefinitely. A determinant plant is a plant whose growth terminates while still under favorable growing conditions. It is opposed to an indeterminate plant whose growth continues while growing conditions are favorable. In one embodiment, the pepper plant ideotype of the present invention has determinate growth when compared to indeterminate growth of non-ideotype pepper plants.

As used herein, the phrase "internode length" refers to the distance between two branching nodes. In one embodiment, the pepper plant ideotype of the present invention has an internode length that is less than 8.5 cm.

The machine harvestable pepper ideotype according to the present invention is suitable for a one time destructive harvesting of an entire planting. The ideotype of the present invention allows the plants to be physically cut on the ground, moved to the bin, shaken to detach fruits from plant, after which the plants can be tossed on the ground.

When the tomato harvester is used for harvesting pepper, it cuts the plants grabs it upside down and shakes it violently. While not wishing to be bound by any theories, we hypothesize that larger fruits produce higher momentum, causing easier detachment. Also, we hypothesized that fruit with thick walls can better withstand physical breakage in the process.

According to the present invention, any processing varieties of pepper used in mechanical harvesting must have easy destemming, which refers to minimum force required to remove the pedicel from the fruit. We hypothesize that the cell type and organization of cells at the fruit and receptacle junction helps determine the detachment force and that the presence of fewer numbers of sclerified cells at the detachment area reduces the destemming force. See, e.g., Marshal, 1998.

Example 2. Development of a Machine Harvestable Sweet Jalapeño Pepper

A: Development of S5017

A cross was made between inbred line 'H78-1R#12' (P1, female) and 'S6M3455B-08-1-1-B' (P2, male) to produce hybrid 'S5017' (F1). A photograph of a representative plant of 'S5017' is provided in FIG. 2.

P1 produces branches prior to bifurcation with wide crotch angle. Absence of distinct bifurcated branching pattern results in the plants having a very short interval between branches. Each lateral branch in-turn develops a bifurcated branching pattern.

P2 has a strong trunk with clear bifurcated branching pattern. The crotch angles in P2 are much narrower as compared to P1 resulting in the plants having a more upright plant habit.

The F1 seed was planted and the resultant F1 plants had a strong, distinct trunk similar to that of the P2 plants. Furthermore, the F1 plants had no clear bifurcation branching pattern on the main stem; rather, they produced several side branches with very wide crotch angles. This resulted in the F1 plants having an umbrella-shaped plant structure. This umbrella-shaped plant structure facilitated synchronized fruit maturity. The time interval between first and last fruiting on the F1 plants was relatively shorter than that for the parents so that all the fruits on the F1 plants attained harvest maturity more or less at the same time.

The resultant pepper F1 plants had at least the following combination of characteristics for the following traits that result in it being a machine harvestable pepper plant ideotype: a determinate growth habit, a pepper yield at least 19% higher than the pepper yield of a check variety of the same type; greater than 3 pre-bifurcation branches at maturity; and a canopy angle greater than 65 degrees at maturity. 'S5017' also had a width to height ratio greater than 0.9 at maturity, greater than 80% matured fruits at harvest time, a percentage of fruits in plant after harvest <0.4%, a fruit concentration greater than 0.15 lbs/inch and other desired agronomical/horticulturally desired traits, such as a branching angle >40 degrees, an internode length <8.5 cm, a pod detachment force <30N, a fruit weight from 5 plants >15 lb, a commercially acceptable fruit weight between 50 g and 80 g, a percentage of yield to biomass >75%, a weight of fruits on the ground <20lb, a percentage of fruits on the ground <9%, a percentage of broken fruits <5%, a wall thickness comprised between 5 to 6.5 mm, a percentage of destemming >50%, a percentage of harvest efficiency in bins >80%, and a percentage of total harvest efficiency >90%.

Plants of 'S5017' produce very strong, short stems (FIG. 2). Unlike, conventional bifurcation branching with indeterminate growth, 'S5017' produces branches with wide crotch angle below the bifurcation point. Several lateral branches develop in a short interval and grow almost horizontally producing unique umbrella shaped determinant plants. Since most of the lateral branches develop in a short time and short vertical space interval, the fruits set on these branches tended to mature at the same time.

'S5017' has large pendent fruits with low pod detachment force which helps ensure separation of fruits from the plants as the harvester applies shaking force to the plants. The processor requires destemmed fruits to be delivered on the plant. So, growers have to set up an assembly line of destemming crew on the harvester or at the packaging shade. Easy destemming variety reduces this labor cost significantly.

B: Development of S5082

A cross was made between inbred line S6M3392B-07-1-1-B (P1, female) and S5M3099B-01-1-2-B (P2, male) to produce hybrid 'S5082' (F1).

P1 produces strong sturdy plants with branches prior to bifurcation with wide crotch angle. The plants have a high branching density and an easy destemming.

P2 produced strong upright plants.

The F1 seed was planted and the resultant F1 plants had a strong, distinct trunk similar to that of the P2 plants. Furthermore, the F1 plants had no clear bifurcation branching pattern on the main stem; rather, they produced several side branches with very wide crotch angles. This resulted in the F1 plants having an umbrella-shaped plant structure. This umbrella-shaped plant structure facilitated synchronized fruit maturity. The time interval between first and last fruiting on the F1 plants was relatively shorter than that for the parents so that all the fruits on the F1 plants attained harvest maturity more or less at the same time.

The resultant pepper F1 plants had at least the following combination of characteristics for the following traits that result in it being a machine harvestable pepper plant ideotype: a determinate growth habit, a pepper yield at least 19% higher than the pepper yield of a check variety of the same type; greater than 3 pre-bifurcation branches at maturity; and a canopy angle greater than 65° at maturity. 'S5082' also had a percentage of fruits intact in the plant after harvest <0.4%, a width to height ratio >0.9 at maturity, a percentage of matured fruits >80% at harvest time, and other desired agronomical/horticulturally desired traits, such as a branching angle >40 degrees, an internode length <8.5 cm, a pod detachment force <30N, a fruit weight from 5 plants >15 lb, a commercially acceptable fruit weight between 50 g and 80 g, a percentage of yield to biomass >75%, a weight of fruits on the ground <20lb, a percentage of fruits on the ground <9%, a percentage of broken fruits <5%, a wall thickness comprised between 5 to 6.5 mm, a percentage of destemming >50%, a percentage of harvest efficiency in bins >80%, a percentage of total harvest efficiency >90%.

Plants of 'S5082' produce very strong, short stems. Unlike, conventional bifurcation branching with indeterminate growth, 'S5082' produces branches with wide crotch angle below the bifurcation point. Several lateral branches develop in a short interval and grow almost horizontally producing unique umbrella shaped determinant plants. Since most of the lateral branches develop in a short time and short vertical space interval, the fruits set on these branches tended to mature at the same time.

'S5082' has large pendent fruits with low pod detachment force which helps ensure separation of fruits from the plants as the harvester applies shaking force to the plants. The processor requires destemmed fruits to be delivered on the plant. So, growers have to set up an assembly line of destemming crew on the harvester or at the packaging shade. Easy destemming variety reduces this labor cost significantly.

Example 3. Harvest Trials

'S5017' and 'S5082' are two representative sweet Jalapeño varieties developed according to the present invention, wherein each variety has the machine harvest pepper plant ideotype of the present invention.

'S5017' and 'S5082' were evaluated in a machine harvest observational field trials in Davis, Calif. The trial was field planted on May and harvested from September depending on the variety. The season was relatively cool for the area but otherwise conditions were normal. The results of this trial are provided in Table 1.

TABLE 1

Results for machine harvest trial in Davis, CA.

| Variety | Fruit Weight (lbs/100 fruits) | # Intact Pedicel/ 100 Fruits | Fruit on the Ground (lbs/30 fruits) | % Fruits on the Ground | Intact Fruits Left on the Plant (lbs/ 10 plants) | % Intact Fruit Left on Plants | Total Yield (tons per acre) |
|---|---|---|---|---|---|---|---|
| S5017 | 15 | 41 | 14.5 | 0.085 | 1.5 | 0.052 | 23.55 |
| S5082 | 12 | 37 | 19 | 0.137 | 1 | 0.043 | 19.25 |
| P115 (check variety) | 12 | 55 | 20 | 0.14 | 1 | 0.044 | 18.81 |
| P105 (check variety) | 12.5 | 46 | 17 | 0.127 | 1 | 0.045 | 18.52 |

The machine harvestable varieties of the present invention allow growers to use tomato harvesters for picking fresh pepper pods from the field. This is one time destructive harvest and the tomato harvester was able to pick 95% of fruits off of the plant.

Furthermore, a trial was also conducted using manual shaking to simulate machine harvest. Three shakings was enough to get all the fruits off of the machine harvest ideotype pepper plants of the present invention.

Example 4. Larger Scale Field Trials

The phenotypic traits and machine harvestablity of the pepper plants of the present invention were compared against standard check pepper varieties in larger scale field trials. The commercially available 'Mammoth' pepper variety was used as a check variety for its phenotypes of tall plant structure, indeterminate plant growth, and high pod detachment force. Variety P115 was used as a secondary check variety for its low pod detachment force and semi-determinate growth pattern.

These check varieties were compared against the 55017 and 55082 pepper varieties of the present invention described in Example 2. Three hundred peppers plants of all four varieties variety were planted in a test plot in Davis, Calif. The trial was conducted during a regular growth season planted on May 22, 2013 and harvested on Sep. 5, 2013. Peppers were harvested at 107 days after transplanting.

Pre-Harvest Assessment

A week prior to harvesting, the plants of all four varieties were analyzed for a variety of phenotypes (Table 2) including:

Determinacy—was assessed visually by comparing the growth and development of the pepper plants at throughout favorably growing conditions. Definitions for determinate and indeterminate growth were as previously described.

Canopy Angle (CANG)—corresponds to the angle from the main stem at the ground level to the sides of the widest point of the plant width. Canopy angle is presented as an average of at least 5 measurements from 5 randomly selected plants.

Matured Fruit Percentage ~100 days (MATFRTPC)—corresponds to the number of matured fruits as a percentage of all pepper fruits on the plants. Percentage was calculated based on fruit counts for all growing plants of a particular variety. Maturity was determined by visually inspecting collected fruits. Mature peppers were defined as peppers having reached their mature firmness, size, and shape expected for their variety for their intended market. Mature peppers did not have to exhibit color changes to be considered mature.

Fruit Concentration (FRTCONC)—was determined by measuring the height of each plant from the soil level to the highest point of each plant and then weighing the fruits produced by said plant. Fruit concentration is then presented as pounds of fruit per inch of height (lb/inch). Fruit concentration represents an average of at least five measurements from five randomly selected plants.

Plant Height (HT)—was measured vertically from the base of the stem at soil level to the most apical portion of the plant. Height was measured in inches. Height is presented as an average of at least five measurements from five randomly selected plants.

Plant Width (WIDE)—was measured as the widest horizontal point of the plant. Width was measured inches. Width is presented as an average of at least five measurements from five randomly selected plants.

Width to Height Ratio (WTHRATIO)—was calculated by dividing the plant width (as defined above), by plant height (as defined above).

Plant Branching Angle (BANG)—was defined as the angle between a branch and its sub-branch, or a stem and the branch arising from the stem. Measurements presented in arc degrees (degree or °). Branching angle is presented as an average of at least five measurements from each of the five randomly selected plants (one branch per plant).

Internode Length (INODE)—was measured as the distance between two nodes. Measurements are presented in centimeters (cm). Internode length is presented as an average of at least five randomly selected plants.

Pod Detachment Force (PDF)—mature peppers were attached to a digital force gauge through a strap, netting, or hook. PDF was measured by slowly pulling the force gauge (with the pepper attached) until the pepper detached from the plant. Maximum force before detachment was recorded in Newtons per fruit (N) where 1 Newton is equivalent to the force of the Earth's gravity on a mass of about 102 grams (Force=mass×acceleration). PDF is presented as an average of at least five measurements from each of the five randomly selected plants.

Biomass From Five Plants (BIOSPL)—five random pepper plants were harvested by cutting the base of the main stem at ground level. Each plant with its pepper fruits still attached, was weighed. Weights are presented in pounds (lb).

Fruit Weight From Five Plants (SPLFRWT)—pepper fruits from five randomly selected plants for each variety were harvested and weighed. Results presented in pounds (lb).

Yield to Biomass Percent (YTBIOM)—was calculated by dividing the plant fruit weight (as defined above), by plant biomass (as defined above) and multiplying the total by 100. Results were presented as a percent (%) of total biomass.

Pepper varieties S5017 and S5082, produced according to the present invention exhibited determinate growth phenotypes with relative homogenous plant sizes pre harvest, i.e. the plants cease vertical growth before flowering resulting into umbrella shaped plants.

Pepper varieties S5017 and S5082 also exhibited increased canopy angles which were hypothesized to improve harvesting efficiency by raising pepper fruits higher off the ground. Additionally, the pepper varieties of the present invention also showed increased fruit concentration values which were expected to produce more compact plants with higher yield for machine harvesting.

Mechanical Harvesting Trial

Test pepper fields at Davis were then harvested using tomato mechanical harvester UC-Blackwelder tomato harvester with two-weight brush shaker system (Blackwelder Manufacturing, Rio Vista, Calif.). This model of harvester first cuts the plants, grabs it upside down and shakes it violently.

After harvesting, the suitability of each variety for the purposes of mechanical harvesting was assessed by quantifying various yield and fruit quality factors as described below and the results shown in Table 3:

Yield—measured by weighing total pepper fruit harvest from each variety and dividing it by total acreage planted with said variety. Results were presented as tons of fruit per acre (t/a).

Pre-Bifurcation Branches (CT)—are defined as branches developing prior to first branch bifurcation (division/splitting of branches into lateral branches). Pre-bifurcation branches are those branches developing directly from the main stem. Higher numbers of pre-bifurcation branches are associated with higher fruit concentrations and higher yields for determinant growth plants. Higher number of pre-bifurcation branches is also associated with higher yield to biomass ratios or percents.

Intact Fruits Remaining on Plants (INTACTPC)—was calculated by harvesting pepper fruits still attached to plant after mechanical harvesting and weighing them. The weight of the intact fruits was then divided by the total pepper fruit yield for a variety including attached fruit, harvested fruit in bins, harvested fruit on ground, and damaged fruit. Results presented as percentage (%) of total fruit weight yield.

Fruits in Bin (FRTBIN)—was measured by weighing the fruits collected into the bins of the mechanical harvester. Results presented in pounds (lbs).

Fruits on the Ground (FRTGRND)—was calculated by weighing the undamaged fruits found on the ground after mechanical harvesting of the pepper plants. Damaged fruits were weighed separately. Results presented in pounds (lbs).

Fruits on the Ground Percentage (FRTGRNDPC)—the weight of fruits on the ground as described above was divided by the total pepper fruit yield for each variety including attached fruit, harvested fruit in bins, and harvested fruit on ground. Results presented as percentage (%) of total fruit weight yield.

Broken Fruits (BROKENPC) (% broken fruits (damaged) were estimated from a sample of 5 lb fruits taken out of the bin Results presented as percentage (%) of total fruit weight yield as described for INTACTPC above.

Pepper Fruit Wall Thickness (WTHICK)—was measured by cutting open pepper fruits and measuring the thickness of the outer fruit wall (pericarp). Measurements were taken using digital vernier calipers. Wall thickness is presented in millimeters (mm). Wall thickness is presented as an average of at least 10 mature pepper fruits.

Pepper Fruit Weight (FRTWT)—was measured by randomly selecting one-hundred mature pepper fruits and weighing them. Total weight was divided by number of fruits weighed to obtain average fruit weight in grams (g).

Harvest Efficiency in Bins (HARVEFF1)—was calculated by dividing the fruits on the bin by total fruits and expressing in percentage.

Total Harvest Efficiency (HARVEFF2)—was calculated by dividing the weight of harvested pepper fruits in bin and on the ground and dividing it by the total fruit weight yield as described above. Results presented as a percent (%).

Harvesting efficiency for all varieties was within a few percentage points. However, the pepper varieties S5017 and S5082 created according to the present invention exhibited much higher yields (37.76 t/a, and 33.93 t/a respectively) than that of the check varieties (24.46 t/a and 28.41 t/a). This was in part due to the determinate plant habit of the pepper varieties of the present invention which allowed for increased fruit concentration and yield which could be mechanically harvested.

This increase in yield was found to be statistically significant after conducting Analysis of Variance (ANOVA, Tables 4 and 5). Similarly statistical analysis of pre-bifurcation branches (Tables 6 and 7), and canopy angle (Tables 8 and 9) proved the distinctness of the new pepper varieties developed according to the present invention.

TABLE 2

Pre-harvest data collected from Davis field pepper trials 2013.

| Variety | Determinacy | CANG (degree) | WTRATIO | MATFRTPC (%) | FRTCONC (lb/inch) | HT (inch) | WIDE (inch |
|---|---|---|---|---|---|---|---|
| Mammoth | Indeterminate | 48.83 | 0.68 | 80.4 | 0.099 | 30 | 20.4 |
| P115 | Semi-determinate | 63.99 | 1.21 | 84.51 | 0.2 | 20 | 24.2 |
| S5017 | Determinate | 81.63 | 0.96 | 83.28 | 0.178 | 19.6 | 18.8 |
| S5082 | Determinate | 66.19 | 1.17 | 87.6 | 0.13 | 20.6 | 24 |

| Variety | BANG (degree) | INODE (cm) | PDF (Newton) | BIO5PL (lb) | 5PLFRWT (lb) | YTBIOM |
|---|---|---|---|---|---|---|
| Mammoth | 44.07 | 7.3 | 24.54 | 19.3 | 14.8 | 77.11 |
| P115 | 37.47 | 7.57 | 22.26 | 24.38 | 20 | 82.07 |
| S5017 | 50 | 8.27 | 28.48 | 31.64 | 26.3 | 83.05 |
| S5082 | 41.17 | 7.19 | 19.16 | 23.4 | 18.3 | 78.3 |

TABLE 3

Post-harvest data collected from Davis Field pepper trials 2013 after mechanical harvest.

| Variety | YIELD (t/a) | CT | INTACTPC (%) | FRTBIN (lb) | FRTGRND (lb) | FRTGRNDPC (%) |
|---|---|---|---|---|---|---|
| Mammoth | 24.46 | 1 | 0.4 | 152.73 | 14.76 | 9.09 |
| P115 | 28.41 | 5 | 0.57 | 177.16 | 17.11 | 8.76 |
| S5017 | 37.76 | 3.4 | 0.38 | 242.33 | 16.41 | 6.28 |
| S5082 | 33.93 | 3.5 | 0.34 | 212.56 | 19.97 | 8.78 |

| Variety | BROKENPC (%) | WTHICK (mm) | DSTMPC (%) | FRTWT (g) | HARVEFF1 (%) | HARVEFF2 (%) |
|---|---|---|---|---|---|---|
| Mammoth | 2.6 | 63.71 | 13.33 | 61.08 | 84.55 | 93.39 |
| P115 | 5.21 | 62.54 | 90 | 67.74 | 80.93 | 89.19 |
| S5017 | 4.88 | 64.46 | 56.67 | 76.81 | 85.42 | 91.47 |
| S5082 | 1.47 | 56.78 | 70 | 56.85 | 86.55 | 95.08 |

TABLE 4

ANOVA of yield in Davis field pepper trials 2013.

| Source | DF | Sum of squares | Mean squares | F | Pr > F |
|---|---|---|---|---|---|
| Model | 4 | 339.11 | 84.78 | 14.77 | 0.000 |
| Error | 10 | 57.41 | 5.74 | | |
| Corrected Total | 14 | 396.52 | | | |

TABLE 5

ANOVA mean separation of yield in Davis field pepper trials 2013.

| Varieties | LS means | Groups | |
|---|---|---|---|
| Mammoth | 24.460 | A | |
| P115 | 28.409 | A | |
| S5082 | 33.932 | | B |
| S5017 | 37.765 | | B |

TABLE 6

ANOVA of pre-bifurcation branches in Davis field pepper trials 2013.

| Source | DF | Sum of squares | Mean squares | F | Pr > F |
|---|---|---|---|---|---|
| Model | 5 | 89.48 | 17.897 | 10.162 | <0.0001 |
| Error | 54 | 95.10 | 1.761 | | |
| Corrected Total | 59 | 184.58 | | | |

TABLE 7

ANOVA mean separation of pre-bifurcation branches in Davis field pepper trials 2013.

| Varieties | LS means | Groups | | |
|---|---|---|---|---|
| Mammoth | 1.000 | A | | |
| P115 | 5.000 | | | D |
| S5082 | 3.500 | | C | |
| S5017 | 3.400 | | B | C |

TABLE 8

ANOVA of canopy angle in Davis field pepper trials 2013.

| Source | DF | Sum of squares | Mean squares | F | Pr > F |
|---|---|---|---|---|---|
| Model | 5 | 5785.88 | 1157.18 | 6.70 | <0.0001 |
| Error | 54 | 9330.10 | 172.78 | | |
| Corrected Total | 159 | 15115.99 | | | |

TABLE 9

ANOVA mean separation of canopy angle in Davis field pepper trials 2013.

| Varieties | LS means | Groups | | |
|---|---|---|---|---|
| Mammoth | 48.83 | A | | |
| P115 | 63.99 | | B | |
| S5082 | 66.19 | | B | |
| S5017 | 81.63 | | | C |

Example 5. Larger Scale Field Trials (Prophetic)

The phenotypic traits and machine harvestablity of the pepper plants of the present invention will be compared against standard, check pepper varieties in larger scale field trials. The commercially available 'Mammoth' pepper variety would make a good check variety as it is a tall, indeterminate type pepper with high pod detachment force.

The field trial could be a randomized complete block design or a split plot design using three replications/repetitions with 10, 20 or 30 plants per replication/repetition. Five or 10 plants/plot could be sampled to account for variation within plot as well as potential genotype×environment (GXE) effects.

Data will be collected as in Example 4 and Table 10.

TABLE 10

Data to be collected in a larger field trial of the machine harvestable pepper plants.

| Trait | Measurement | Procedure |
|---|---|---|
| Resistance to break | % broken fruit | Collect 5 lb sample from bin harvested by machine; measure cracked and split (broken) fruits and calculate the percentage. |
| Branch density | #/cm | Randomly sample 5 plants; measure length from first branch at bottom to last branch at top, and count the number of branches. Express as # of branches per cm. |
| Uniform maturity | % immature fruit | Count # of immature fruits and total fruit on 5 plants and calculate % of marketable fruit. |
| Destemming | Measure force to remove stem in Newton/fruit | Randomly select 100 fruit with stem intact. Remove stem using force measuring machine. Express as average force needed to remove the stem/fruit |
| Fruits on the ground | kg per plant | Collect all the fruits that fall on ground during machine harvest and weigh them in kg |
| Intact stem (pedicel) on the fruits | % intact stems (pedicels) | Randomly select 100 machine harvested fruits from bin and count # of fruit that contain intact pedicel. This is an indirect measure. |

Pepper varieties that could be included in the larger field trials are provided in the following table.

TABLE 11

Pepper varieties to test.

| Variety | Pod Detachment Force | Destemming | Resistance to Break | Internode Length | Branching Angle | Pepper Type |
|---|---|---|---|---|---|---|
| S5017 | Low | Easy | High | Very short | Wide | Sweet Jalapeño |
| S5082 | Low | Easy | High | Very short | Wide | Sweet Jalapeño |
| P115 | Low | Easy | High | Very short | Wide | Sweet Jalapeño* check |
| 5807 | TBD | TBD | TBD | TBD | TBD | Hot Jalapeño check |

TABLE 11-continued

Pepper varieties to test.

| Variety | Pod Detachment Force | Destemming | Resistance to Break | Internode Length | Branching Angle | Pepper Type |
|---|---|---|---|---|---|---|
| 5810 | TBD | TBD | TBD | TBD | TBD | Hot Jalapeño check |
| Bravo | TBD | TBD | TBD | TBD | TBD | Hot Jalapeño check |

*Sweet Jalapeño* is an indeterminate variety and so is not the Ideotype and there is used as a Check.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. It should be understood that the examples and embodiments described herein are for illustrative purposes only and that various modifications or changes in light thereof will be suggested to persons skilled in the art and are to be included within the spirit and purview of this application.

Deposit Information

A deposit of the pepper seeds of this invention is maintained by HM Clause Inc., previously known as Harris Moran Seed Company Davis Research Station, 9241 Mace Boulevard, Davis Calif. 95616.

In addition, a sample of the pepper seeds of this invention has been deposited by HM Clause Inc., previously known as Harris Moran Seed Company, 555 Codoni Avenue, Modesto, Calif. 95357, with the American Type Culture Collection (ATCC) in Manassas, Va. on Mar. 13, 2014. HM Clause Inc., previously known as Harris Moran Seed Company has authorized the applicant to refer to the deposited biological material in the application.

To satisfy the enablement requirements of 35 U.S.C. § 112, and to certify that the deposit of the seeds of the present invention meets the criteria set forth in 37 C.F.R. §§ 1.801-1.809, Applicants hereby make the following statements regarding the deposited pepper seed 'S5017', and 'S5082' (deposited as ATCC Accession Nos. PTA-121088 and PTA-121087, respectively):

1. During the pendency of this application, access to the invention will be afforded to the Commissioner upon request;
2. Upon granting of the patent the seeds will be available to the public under conditions specified in 37 CFR 1.808;
3. The deposit will be maintained in a public repository for a period of 30 years or 5 years after the last request or for the enforceable life of the patent, whichever is longer; and
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same seed source with the ATCC.

ADDITIONAL REFERENCES

Paul A. Funk, Stephanie J. Walker and Ryan P. Herbon. 2011. A Systems Approach to Chile Harvest Mechanization. International Journal of Vegetable Science, 17: 296-309.

Marshall, D. E. and B. N. Boese. 1998. Breeding *Capsicum* for mechanical harvest, Part 2 Equipment. Proc., 10:61-64. 10th Eucarpia Meeting on Genetics and Breeding of *Capsicum* and Eggplant, Avignon, France.

Shifriss, C. and Y. Hakim. 1977. Segregation for prebifurcation shooting, stem length of leaf number of main stem in two crosses of *Capsicum annuum* L. Euphytica. 26: 491-495

Marshall, D. E. and B. N. Boese. 1998. Breeding *Capsicum* for mechanical harvest, Part 2 Genetics. Proc., 10: 41-46. 10th Eucarpia Meeting on Genetics and Breeding of *Capsicum* and Eggplant, Avignon, France.

Carl E. Motsenbocker, 1996. Detachment Force and Fruit Characteristics of Tabasco Pepper at Several Stages of Development. HORTSCIENCE 31(7): 1231-1233

Stall, W. M. 1973. An evaluation of fruit detachment characters in pepper. PhD Diss., Univ. of Florida, Gainesville.

Walker, S., M. M. Wall and P. W. Bosland. 2004. 'NuMex Garnet' Paprika. HortScience, 39(3):629-630.

Paul W. Bosland. 2010. 'NuMex Jalmundo' Jalapeño. HortScience, 45(3):443-444.

The invention claimed is:

1. A seed of a pepper plant, wherein the pepper plant produced from said seed is hybrid pepper plant designated S5017 or hybrid pepper plant designated S5082, wherein a representative sample of S5017 has been deposited under ATCC Accession Number PTA-121088, and a representative sample of S5082 has been deposited under ATCC Accession Number PTA-121087.

2. A pepper plant, or a part thereof or a plant cell thereof, produced by growing the seed of claim 1, wherein a plant regenerated from said plant part or plant cell has all of the morphological and physiological characteristics of pepper plant S5017 or S5082 when grown in the same environmental conditions.

3. The pepper plant, or a part thereof or a plant cell of claim 2, wherein the plant part is a fruit, flowers, roots, a rootstock or a scion.

4. The pepper plant, or a part thereof or a plant cell of claim 2, wherein the plant cell is a regenerable cell.

5. A tissue culture of regenerable cells produced from the plant or plant part of claim 2, wherein a plant regenerated from the tissue culture has all of the morphological and physiological characteristics of pepper plant S5017 or S5082 when grown in the same environmental conditions and wherein a representative sample of the seed of S5017 has been deposited under ATCC Accession Number PTA-121088, and a representative sample of the seed of S5082 has been deposited under ATCC Accession Number PTA-121087.

6. A pepper plant regenerated from the tissue culture of claim 5, said plant having all of the morphological and physiological characteristics of pepper plant S5017 or S5082 when grown in the same environmental conditions, and wherein a representative sample of the seed of S5017 has been deposited under ATCC Accession Number PTA-121088, and a representative sample of the seed of S5082 has been deposited under ATCC Accession Number PTA-121087.

7. A pepper plant fruit produced from the plant of claim 2.

8. A method for producing a pepper seed derived from pepper plant of claim 2, comprising self-pollinating the pepper plant of claim 2 and harvesting the resultant pepper seed.

9. A method for producing a progeny pepper plant derived from pepper plant of claim 2, comprising self-pollinating the pepper plant of claim 2 at least once to produce a progeny pepper plant derived from the plant of claim 2.

10. A method for producing a pepper plant, comprising crossing a first parent pepper plant with a second parent pepper, wherein said first parent pepper plant and/or second parent pepper plant is the pepper plant of claim 2.

11. A method of producing a pepper plant derived from the pepper plant of claim 2, the method comprising the step of:
  (a) crossing the plant of claim 2 with a second pepper plant to produce a progeny plant.

12. The method of claim 11, wherein the method further comprises
  (b) crossing the progeny plant of step (a) with itself or a second pepper plant to produce a seed;
  (c) growing a progeny plant of a subsequent generation from the seed produced in step (b); and
  (d) crossing the progeny plant of a subsequent generation of step (c) with itself or a second pepper plant to produce a pepper plant derived from the pepper plant of claim 2.

13. The method of claim 12, further comprising the step of:
  (e) repeating step b) and/or c) for at least 1 more generation to produce a pepper plant derived from the pepper plant of claim 2.

14. A method of producing pepper fruits, said method comprising:
  a. placing a seed from a pepper plant of claim 2 in an environment conducive to germination,
  b. allowing said seed to germinate into a plant, and
  c. allowing said plant to produce pepper fruits.

15. A method of harvesting peppers, said method comprising harvesting the fruit of a mature pepper plant using a harvesting machine, wherein the mature pepper plant that is harvested is the pepper plant of claim 2.

* * * * *